(12) United States Patent
Sager

(10) Patent No.: US 7,967,606 B2
(45) Date of Patent: Jun. 28, 2011

(54) PROCESS FOR MANUFACTURING CUSTOM CROWN COPINGS AND INFRASTRUCTURES

(76) Inventor: Robert David Sager, Manhattan, KS (US)

( * ) Notice: Subject to any disclaimer, the term of this patent is extended or adjusted under 35 U.S.C. 154(b) by 270 days.

(21) Appl. No.: 12/212,256

(22) Filed: Sep. 17, 2008

(65) Prior Publication Data

US 2009/0186319 A1     Jul. 23, 2009

Related U.S. Application Data

(63) Continuation of application No. 11/023,950, filed on Dec. 28, 2004, now Pat. No. 7,445,449.

(60) Provisional application No. 60/631,102, filed on Nov. 26, 2004, provisional application No. 60/566,855, filed on Apr. 30, 2004, provisional application No. 60/543,038, filed on Feb. 6, 2004.

(51) Int. Cl.
    *A61C 5/10*     (2006.01)
(52) U.S. Cl. .................................. 433/173; 433/223
(58) Field of Classification Search .............. 433/172, 433/173, 174, 213, 214, 218, 223
See application file for complete search history.

(56) References Cited

U.S. PATENT DOCUMENTS

| | | | | |
|---|---|---|---|---|
| 5,527,182 A * | 6/1996 | Willoughby | .................. | 433/172 |
| 5,725,376 A * | 3/1998 | Poirier | .......................... | 433/172 |
| 5,857,853 A * | 1/1999 | van Nifterick et al. | ........ | 433/213 |
| 6,398,554 B1 * | 6/2002 | Perot et al. | ..................... | 433/223 |
| 6,558,162 B1 * | 5/2003 | Porter et al. | .................. | 433/173 |
| 6,568,936 B2 * | 5/2003 | MacDougald et al. | ........ | 433/223 |
| 6,790,040 B2 * | 9/2004 | Amber et al. | ................. | 433/173 |
| 7,234,938 B2 * | 6/2007 | Bodenmiller | ................... | 433/51 |
| 7,445,449 B2 * | 11/2008 | Sager | ........................... | 433/223 |
| 2006/0106484 A1 * | 5/2006 | Saliger et al. | ................. | 700/182 |

* cited by examiner

*Primary Examiner* — Ralph A Lewis
(74) *Attorney, Agent, or Firm* — Bryan P. Stanley; Kutak Rock LLP

(57) ABSTRACT

A method of manufacturing custom crown coping and infrastructures is provided. A metal portion (base) of an abutment is located in a model of a patient's mouth and the model is scanned. The data from the scan is then utilized to manufacture the ceramic portion of the abutment and the coping. In one embodiment, the coping and infrastructure is designed by first determining the shape and orientation of the final crown, subtracting a thickness for the crown from the shape to determine the shape and orientation of a coping, and subtracting a thickness for the coping to form the shape and orientation of an abutment.

12 Claims, 4 Drawing Sheets

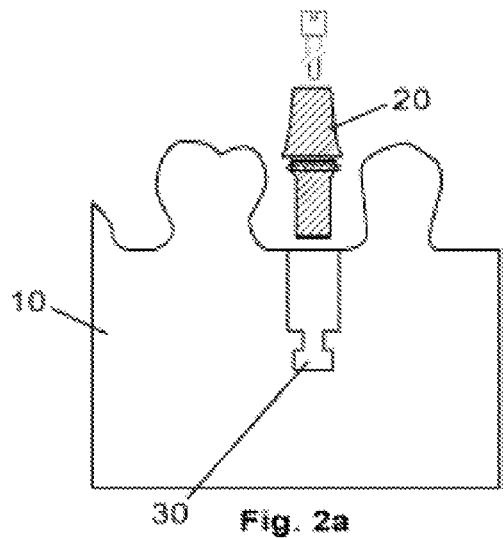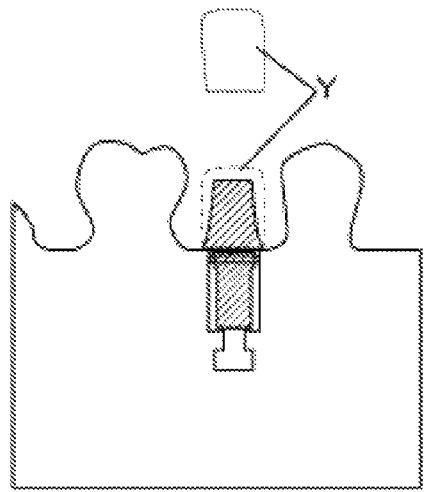
Fig. 2a　　　　　　　　　　　　　　　Fig. 2b
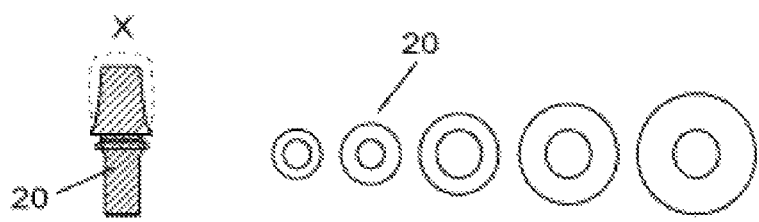
Fig. 3

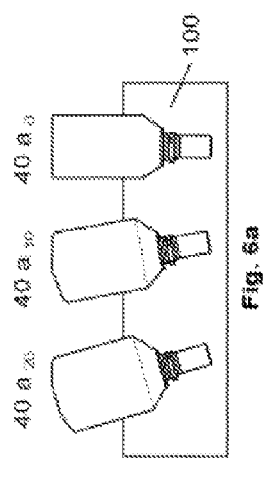
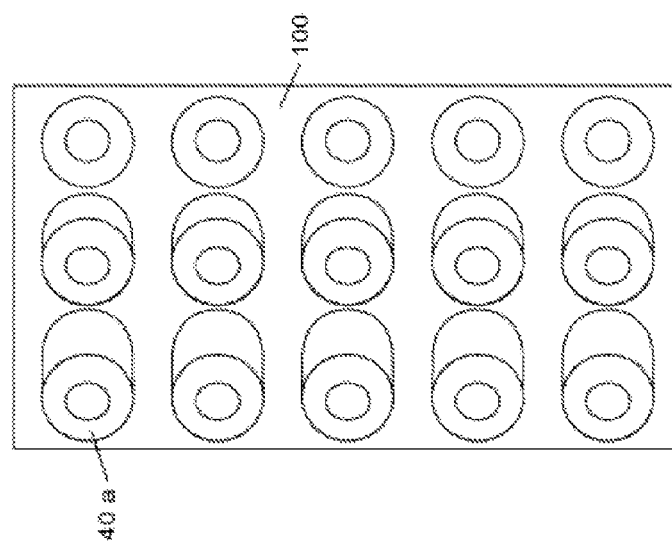

PROCESS FOR MANUFACTURING CUSTOM CROWN COPINGS AND INFRASTRUCTURES

CROSS-REFERENCE TO RELATED APPLICATIONS

This application is a continuation application of U.S. application Ser. No. 11/023,950 filed Dec. 28, 2004, which claims priority pursuant to 35 U.S.C. 119(e) to co-pending U.S. Provisional Patent Application Ser. No. 60/631,102, filed Nov. 26, 2004, U.S. Provisional Patent Application Ser. No. 60/566,855, filed Apr. 30, 2004 and U.S. Provisional Patent Application Ser. No. 60/543,038, filed Feb. 6, 2004, the entire disclosures of which are incorporated herein by reference.

FIELD OF THE INVENTION

The present invention relates generally to prosthodontic systems, methods and apparatuses. More particularly, the present invention is concerned with a process for manufacturing custom dental crown copings and infrastructures which provides economy of manpower, time, materials and machine.

BACKGROUND OF THE INVENTION

Prior to the advent of the instant invention, prosthodontic systems have been extremely labor intensive and time consuming, requiring a considerable amount of skilled labor to custom fit prosthodontics for each case. Examples of a prior art prosthodontic systems include the Lava™ Zirconium CAD/CAM-CNC Crown Coping and Infrastructure System offered by 3M ESPE, and the Camlog Implant System's Ti-Ceramic Abutment. The Lava™ System utilizes a zirconia block which is CNC shaped in a greenware state that is then ceramic infused and heat sintered. The Camlog Implant System and other implant systems, utilize a two-piece abutment comprised of an upper sintered ceramic (zirconia) portion of the abutment that requires modification and a lower metal portion of the abutment that is screw affixed to the implant in the location in which a tooth replacement is necessary in the patient's mouth. The ceramic portion of the abutment, which is cemented to the metal portion in the lab prior to constructing the crown coping, simulates a laboratory analog of a prepared tooth stump base for fabrication of a custom crown coping, such as a Lava™ crown coping. It is noted that crown copings can also be fabricated from built-up powder as in the Vita/Vident Inceram/Zirconium System. It is noted also, all Ceramic crown systems at present require some type of ceramic base coping to be made first and then layered with porcelain to create the highly individualized likeness of the original tooth that is being replaced.

In the present system, when a patient requires a tooth replacement, a three-dimensional stone model of the patient's mouth is prepared from a master impression. If a two-piece abutment such as the Camlog Implant System's Ti-Ceramic Abutment described above is to be utilized, a lab technician will use the model of the patient's mouth to fit the metal portion of the abutment into the appropriate implant analog location in the model. The ceramic portion of the abutment is placed on the metal portion and the technician then modifies the ceramic portion by grinding down the factory sintered Zirconia ceramic piece so that its shape is appropriate for the location and orientation in which it will best support the final crown positioned within the patient's mouth. Once the ceramic portion of the abutment is modified to its final shape, the abutment, which is located in the model, is scanned. Using data from the scan about the shape and orientation of the abutment, as well as the existing teeth surrounding the position of the abutment, the necessary shape of a crown coping is determined and the crown coping is manufactured. In the context of the Lava™ System, a Computer Numeric Control (CNC) milling machine is utilized to manufacture the coping by milling a Lava™ block. Once the coping is completed, and built-up with porcelain to resemble a natural tooth, the entire piece (coping and abutment) is ready for placement in the patient's mouth. The crown coping/crown is cemented conventionally (like any crown to a tooth) to the installed abutment.

The prior art system described above is very time consuming, as it requires a considerable amount of labor and time to modify the abutment and then separately manufacture the coping based upon the shape of the modified abutment. In some cases, the ceramic portion of the abutment requires considerable modification due to its orientation within the patient's mouth such that a relatively small surface of the abutment remains for mounting of the coping. It is noted that a ceramic infiltrated sintered abutment is extremely hard to cut, compared to its greenware stage. In addition, the prior art system results in substantial waste of materials as the ceramic abutment and the coping are manufactured independently and/or by different processes and/or materials. Therefore, it would be beneficial to provide a system for simultaneously manufacturing a custom dental crown coping and ceramic infrastructure (abutment or ceramic portion of the abutment if two piece) to reduce the amount of labor, time and materials.

SUMMARY OF THE INVENTION

A principal object of the instant invention is to provide a system for simultaneously or mechanico-sequentially fabricating a custom dental crown coping and infrastructure (abutment) to reduce the amount of labor, time and materials. The process is accomplished by integrating, sharing and interpreting stored Cad/Cam digital job information and CNC machining programs to achieve optimized custom milling results.

The objects of the instant invention are accomplished through the use of a system that includes a two piece abutment similar to that described above (until such time as the material and process allow one piece ceramic/zirconium abutments). The metal insert portion of the abutment is a standard piece. The ceramic portion of the abutment becomes a custom-made piece, which is manufactured at the same time the coping is manufactured.

When a patient requires a tooth replacement, a three-dimensional model of the patient's mouth is prepared. Using the model of the patient's mouth, a lab technician will fit the metal portion of the abutment into the appropriate location in the model. The model will then be scanned. The scan provides data about the orientation of the metal insert within the model of the mouth and also data about the existing teeth surrounding the position of the abutment. The data from the scan, along with stored data about the standard shape of the metal insert to which the ceramic portion is to be mounted, is used to determine and design the appropriate shape for the ceramic portion of the abutment. At the same time, the shape of the coping is internally designed, using the data so that the coping will fit over the designed ceramic portion of the abutment.

In one embodiment of the instant invention, the ceramic portion of the abutment and the coping are milled in a greenware stage and then sintered. In such an embodiment, it is necessary to shape the ceramic pieces as they are cut in the greenware stage so as to accommodate shrinkage that occurs during the sintering process and to result in a piece of the desired shape and size after sintering. As discussed with respect to the prior art, cutting the ceramic pieces in the greenware stage is much easier to accomplish than cutting once the pieces have been sintered. Nevertheless, the sintering process itself is an additional time consuming step that is required when working with greenware pieces. In an alternative embodiment, the ceramic pieces are milled from a factory sintered block (such as titanium, zirconium, inceram, plastic or any other suitable material now known or later discovered). Cutting of the factory sintered block is slower than cutting from a greenware block; however the additional sintering step is eliminated. The use of a factory sintered block provides additional advantages over the use of a greenware block, such as allowing larger pieces to be milled from a single block (i.e. full arches versus single crowns or bridges).

In a preferred embodiment of the instant invention, in which the ceramic portion of the abutment are milled from a factory sintered block, a custom crown core and custom crown coping is made for use with an off-the-shelf lower abutment portion, such as the lower metal portion (Ti-base) of the Camlog Implant System discussed above. Information regarding the size and shape of the off-the-shelf pieces are stored in a data file or library accessed by a milling machine (such as a DCS milling machine). The Ti-base is placed in a master model implant analog and the model is scanned to obtain data about the orientation of the base within the model and data about the existing teeth surrounding the position of the base within the model. The data from the scan is combined with the stored size and shape information regarding the Ti-base to design a custom crown core part to fit over the Ti-base and a custom crown coping to fit over the custom crown core. The custom crown core will be designed to have predetermined minimum dimensions based upon the size and shape of the Ti-base being used. In most instances however, the actual custom crown core will have dimensions greater than the library-stored "minimum", thus the dimensions of the custom crown core will include a wax-up from the minimum dimensions. Once the final dimensions for the custom crown core and the custom crown coping are determined by wax-up software, the core and coping pieces are milled from a block of material.

In prior art systems, the custom dental crown coping and infrastructure (abutment) are manufactured from the ground up. The abutment is designed first and the coping is designed to fit the abutment. In the instant invention the custom dental crown coping and infrastructure can be manufactured from the ground up by first determining the shape and orientation of the abutment and then determining the shape and orientation of the coping.

Alternatively, the custom dental crown coping and infrastructure of the instant invention can be manufactured from the end product. In such a manner, the model is scanned and the shape and orientation of the final crown is determined or visualized. The thickness for the crown is subtracted to determine the shape and orientation of the coping. The thickness of the coping is then subtracted to form the shape and orientation of the abutment.

The system of the instant invention allows both the coping at the ceramic portion of the abutment to be manufactured from a single block, significantly reducing the amount of material required. In addition, the inventive system significantly reduces the amount of labor necessary to manufacture the coping and the abutment. Because the abutment is custom manufactured, a superior mounting surface is achieved, regardless of the orientation of the metal insert with the mouth.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

FIGS. 2a and 2b are partial front views of a master model implant analog of an embodiment of the instant invention.

FIG. 3 shows front and top views of an implant base portion.

FIGS. 6a and 6b show a DCS frame of an embodiment of the instant invention.

DETAILED DESCRIPTION OF A PREFERRED EMBODIMENT

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
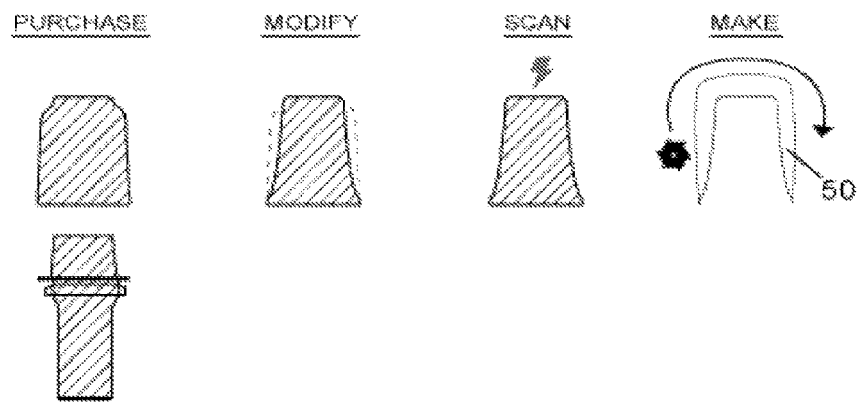
FIG. 1 is a schematic of a method of manufacturing custom crown copings and infrastructures of the prior art.

Referring to FIG. 1 a schematic of a method of manufacturing custom crown copings and infrastructures of the prior art is shown. As is shown in FIG. 1, the manufacturing method of the prior art begins with the purchase of a two piece abutment from a manufacturer. The abutment is located in a model of the patient's mouth and the ceramic portion of the abutment is then modified by a technician to a shape that is appropriate for the location and orientation in the patient's mount. Once the ceramic portion of the abutment is modified to its final shape, the abutment, which is located in the model, is scanned. The data from the scan about the shape and orientation of the abutment, as well as the existing teeth surrounding the position of the abutment, is then used to manufacture a crown coping.

Figure 2:
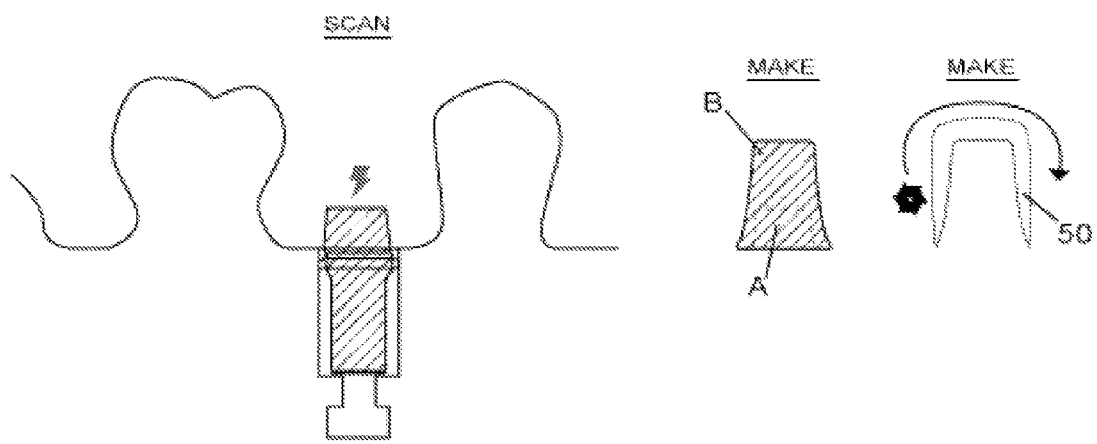
FIG. 2 is a schematic of the method of manufacturing custom crown copings and infrastructures of the instant invention.
Figure 4:
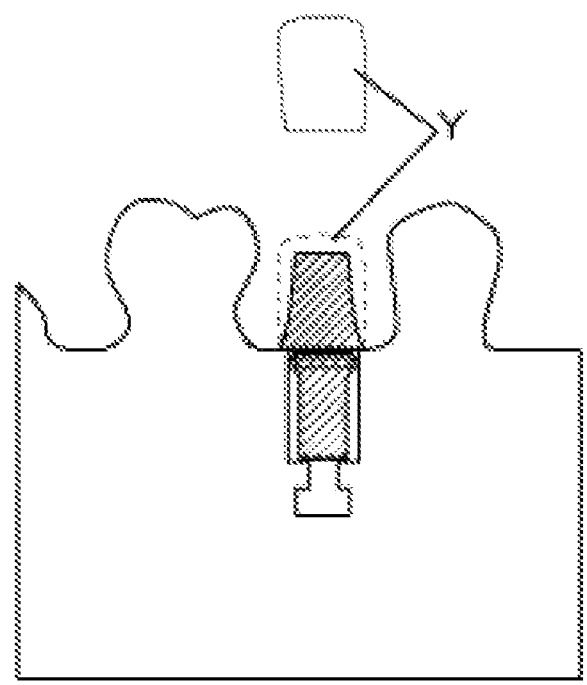
FIG. 4 shows a core of an embodiment of the instant invention designed within the master model implant analog of FIGS. 2a and 2b.
Figure 5:
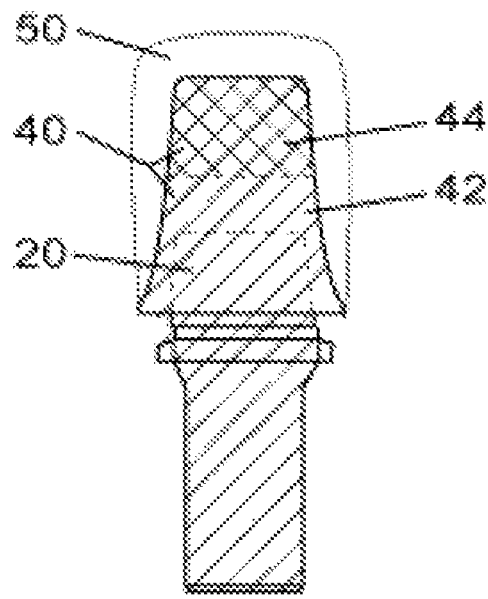
FIG. 5 shows the core of FIG. 4 and a coping designed to fit over the core.

Referring to FIG. 2 is a schematic of the method of manufacturing custom crown copings and infrastructures of the instant invention. As is shown in FIG. 2, the manufacturing method of the instant invention begins with the purchase of the metal portion of the abutment from a manufacturer. The abutment is located in a model of the patient's mouth and the metal portion of the abutment, which is located in the model, is scanned. The data from the scan is then utilized to manufacture the ceramic portion of the abutment and the coping.

As is shown in FIGS. 2a and 2b, when a patient requires a tooth replacement, a three-dimensional model 10 of the patient's mouth is prepared. Using the model of the patient's mouth, a lab technician will fit the metal portion 20 of the abutment into the appropriate location 30 in the model. The model will then be scanned. The scan provides data about the orientation of the metal insert within the model of the mouth and also data about the existing teeth surrounding the position of the abutment. The data from the scan, along with stored data about the standard shape of the metal insert to which the ceramic portion is to be mounted, is used to determine and design the appropriate shape for the ceramic portion of the abutment. At the same time, the shape of the coping is internally designed, using the data so that the coping will fit over the designed ceramic portion of the abutment.

Referring to FIGS. 2a, 2b, 3, 4 and 5, the process of manufacturing a custom crown core and custom crown coping from a factory sintered block is shown. In the embodiment shown, the custom crown core and custom crown coping is made for use with an off-the-shelf lower abutment portion, such as the lower metal portion (Ti-base) of the Camlog Implant System. Information regarding the size and shape (X) of the off-the-shelf pieces are stored in a data file or library accessed by a milling machine (such as a DCS milling machine). For example, as is shown in FIG. 3, information regarding size and shape X for five diameters of implants is shown. The Ti-base 20 is placed in a master model implant analog 10 and the model is scanned to obtain data about the orientation of the base within the model (such as the 3-dimensional axis) and data about the existing teeth surrounding the position of the base within the model (such as the interdental/arch Y information). The data from the scan, Y, is combined with the stored size and shape information regarding the Ti-base, X, to design a custom crown core part 40 to fit over the Ti-base 20 and a custom crown coping 50 to fit over the custom crown core. The custom crown core will be designed to have predetermined minimum dimensions 42 (stored in library) based upon the size and shape of the Ti-base being used. In most instances however, the actual custom crown core will have dimensions greater than the library-stored "minimum", thus the dimensions of the custom crown core 40 will include a wax-up 44 from the minimum dimensions 42. Once the final dimensions for the custom crown core 40 and the custom crown coping 50 are determined by wax-up software, the core and coping pieces are milled from a block of material.

In an alternative embodiment, rather than milling core 40 and coping 50 from a single block of material, the core and coping may be milled out of separate pieces of material. Referring to FIGS. 6a and 6b, one such embodiment is shown and described, in which the material for the core 40 is retained within a frame 100 for support during milling. Frame 100 is designed for use in a single axis milling machine, such as a DCS milling machine, to accomplish milling of custom crown cores. Frame 100 includes a molded/milled polymer base 110 which holds a threaded base 120 to which a blank 40a for the custom crown core 40 is attached. The frame is placed within the milling machine, and one of three angled blanks is chosen by control software of the machine depending upon the desired shape of the custom crown core 40 that is to be machined. This allows for undercutting of the blank which may be necessary for custom crown cores that will be located at a variety of angled orientations. Implants having a generally orthogonal orientation will generally utilize the 0 degree blank, $40a_0$, for milling. As the orientation angle increases to about 10 decrees from an orthogonal orientation, the 10 decree blank, $40a_{10}$, will be utilized. As the orientation angle increases to about 20 degrees from an orthogonal orientation, the 20 decree blank, $40a_{20}$, will be utilized. Because additional material is needed to provide the "minimum" dimension of the custom core in angled orientations, the diameters of the blanks increase as the angle increases (i.e. 10 degree blank is larger diameter than 0 degree blank, and 20 degree blank is larger diameter than 10 degree blank). Once custom crown core 40 milled, the design file is utilized to mill the coping from a separate block of material.

Once crown core 40 and coping 50 are milled, whether from a single piece of material, or from separate pieces, core 40 and coping 50 are hand finished.

In prior art systems, the custom dental crown coping and infrastructure (abutment) are manufactured from the ground up. The abutment is designed first and the coping is designed to fit the abutment. In the instant invention the custom dental crown coping and infrastructure can be manufactured from the ground up by first determining the shape and orientation of the abutment and then determining the shape and orientation of the coping.

Alternatively, the custom dental crown coping and infrastructure of the instant invention can be manufactured from the end product. In such a manner, the model is scanned and the shape and orientation of the final crown is determined or visualized. The thickness for the crown is subtracted to determine the shape and orientation of the coping. The thickness of the coping is then subtracted to form the shape and orientation of the abutment.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A method of manufacturing custom crown copings and infrastructures comprising the steps of:
    preparing a three-dimensional model of a patient's mouth;
    fitting an implant abutment insert into the model;
    storing data about the implant abutment insert standard size and shape in a file;
    scanning the model while the implant abutment insert is in the model;
    utilizing the implant abutment insert size data and data from said scanning step to determine and design a core to fit over the insert and at the same time determine and design a coping to fit over the core; and
    manufacturing said core and said coping.

2. The method as claimed in claim 1 further comprising the step of milling the core and the coping from a material.

3. The method as claimed in claim 2 wherein the material is a factory sintered material.

4. The method as claimed in claim 2 wherein the material is a single block of material.

5. The method as claimed in claim 2 wherein the material comprises a core blank material and a coping block material.

6. The method as claimed in claim 5 further comprising the step of placing the core blank material within a frame.

7. The method as claimed in claim 6 wherein the frame includes multiple orientation options for the blank.

8. The method as claimed in claim 1 wherein the core includes a predetermined minimum dimension.

9. The method as claimed in claim 8 wherein the core includes a wax-up from said minimum dimension.

10. The method as claimed in claim 1 wherein said utilizing step comprises the steps of:
    designing the core; and
    designing the coping to fit over the core once the core is designed.

11. The method as claimed in claim 1 wherein said utilizing step comprises the steps of:
    determining a shape of a final crown based upon data obtained from said scanning step;
    subtracting a thickness of the crown from the crown shape to determine a shape and orientation of a coping; and
    subtracting a thickness of the coping from the coping shape to form a shape and orientation of the core.

12. A method of manufacturing custom crown copings and infrastructures comprising the steps of:
    preparing a three-dimensional model of a patient's mouth;
    determining a shape of a final crown based upon data obtained from said three dimensional model of said patient's mouth;
    subtracting a thickness of the crown from the crown shape to determine a shape and orientation of a coping;
    subtracting a thickness of the coping from the coping shape to form a shape and orientation of the core;
    manufacturing said coping based upon said determined shape and orientation of said coping; and
    manufacturing said core based upon said determined shape and orientation of said core.

* * * * *